(12) United States Patent
Gamwo et al.

(10) Patent No.: US 7,619,011 B1
(45) Date of Patent: Nov. 17, 2009

(54) DESIGN OF SLURRY BUBBLE COLUMN REACTORS: NOVEL TECHNIQUE FOR OPTIMUM CATALYST SIZE SELECTION CONTRACTUAL ORIGIN OF THE INVENTION

(75) Inventors: Isaac K. Gamwo, Murrysville, PA (US); Dimitri Gidaspow, Northbrook, IL (US); Jonghwun Jung, Naperville, IL (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 699 days.

(21) Appl. No.: 11/366,452

(22) Filed: Mar. 3, 2006

(51) Int. Cl.
*C07C 27/00* (2006.01)
(52) U.S. Cl. ...................................... 518/700; 518/728
(58) Field of Classification Search .................. 518/700, 518/728
See application file for complete search history.

(56) References Cited

U.S. PATENT DOCUMENTS

| | | | |
|---|---|---|---|
| 5,348,982 A * | 9/1994 | Herbolzheimer et al. | 518/700 |
| 2005/0209350 A1 * | 9/2005 | Espinoza et al. | 518/726 |
| 2007/0003450 A1 * | 1/2007 | Burdett et al. | 422/108 |

* cited by examiner

*Primary Examiner*—Jafar Parsa
(74) *Attorney, Agent, or Firm*—James B. Potts; Bradley W. Smith; Paul A. Gottlieb

(57) ABSTRACT

A method for determining optimum catalyst particle size for a gas-solid, liquid-solid, or gas-liquid-solid fluidized bed reactor such as a slurry bubble column reactor (SBCR) for converting synthesis gas into liquid fuels considers the complete granular temperature balance based on the kinetic theory of granular flow, the effect of a volumetric mass transfer coefficient between the liquid and the gas, and the water gas shift reaction. The granular temperature of the catalyst particles representing the kinetic energy of the catalyst particles is measured and the volumetric mass transfer coefficient between the gas and liquid phases is calculated using the granular temperature. Catalyst particle size is varied from 20 μm to 120 μm and a maximum mass transfer coefficient corresponding to optimum liquid hydrocarbon fuel production is determined. Optimum catalyst particle size for maximum methanol production in a SBCR was determined to be in the range of 60-70 μm.

19 Claims, 15 Drawing Sheets
(5 of 15 Drawing Sheet(s) Filed in Color)

Large and Small Scales Oscillations for Axial Velocity of Solid As a Function of Time at x=15.5cm, y=11.5cm of Two-Dimensional Viscosity Input Model Optimum Particle Size for Mixing (Maximum Granular-like Temperature) in the IIT Slurry Bubble Column. ($V_L$=2.02cm/s, $V_G$=3.37cm/s)

dp : Particle Diameter
$\delta_c$ : Concentration Boundary Layer Thickness
$\delta_m$ : Momentum Boundary Layer Thickness Concentration and Momentum Boundary Layers in a Slurry Bubble Column Reactor. It is assumed that the liquid layer surrounds the particles Mass Transfer Coefficient Obtained from Computed Granular-likeTemperatures of Figure 3

Volumetric Mass Transfer Coefficient Based on Effective
Particle Diameter Using Coagulation Theory

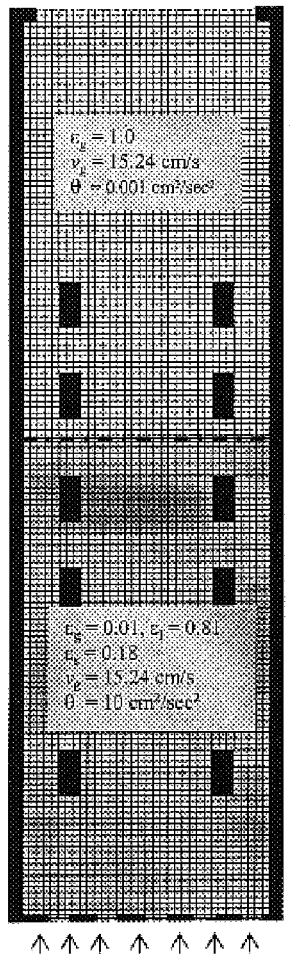

| Initial Conditions and System Properties | |
|---|---|
| Diamter of Reactor (cm) | 57 |
| Height of Reactor (cm) | 813 |
| Temperature (°C) | 250.3 |
| Pressure (psig) | 753.2 |
| Inlet Gas Velocity (cm/sec) | 15.24 |
| Inlet Liquid Velocity (cm/sec) | 0.0 |
| Inlet Catalyst Velocity (cm/sec) | 0.0 |
| Diameter of Catalyst (μm) | 50 |
| Density of Catalyst (Kg/m$^3$) | 3011 |
| Liquid | Wax |
| Density of Liquid (Kg/m$^3$) | 851.5 |
| Restitution Coefficient ($e$) | 0.9995 |
| Wall Restitution Coefficient ($e_w$) | 0.95 |
| Specularity Coefficient ($\Phi$) | 0.6 |
| Time Interval (sec) | $1.0 \times 10^{-4}$ |
| Grid Size (Dx × Dy) (cm) | 1.677 × 5.082 |
| Number of Cell | 34 × 160 |

Figure 7.
Initial and Boundary Conditions for Methanol Synthesis

Computed Gas (A) and Liquid (B) holdup Averaged from 15 to 30 seconds in the Simulation of LaPorte's Methanol Synthesis Using the Kinetic Theory (The color bar shows the range of gas and liquid volume fractions)

Computed Catalyst (Solids) Volume Fraction and Catalyst (Solids) Flow Pattern Averaged from 15 to 30 seconds in the Simulation of LaPorte's Methanol Synthesis Using the Kinetic Theory Granular Temperature (A) and Catalyst Shear Viscosity (B)
Averaged from 15 to 30 seconds in the Simulation of LaPorte's
Methanol Synthesis Using the Kinetic Theory Computed Mole Fraction of Methanol (A) and Water (B) in the Gas Phase Averaged from 15 to 30 seconds in the Simulation of LaPorte's Methanol Synthesis Using the Kinetic Theory Computed Mole Fraction of Methanol (A) and Water (B) in the Liquid Phase Averaged from 15 to 30 seconds in the Simulation of LaPorte's Methanol Synthesis Using the Kinetic Theory Methanol Production and Granular Temperature Obtained from the Different Volumetric Mass Transfer Coefficients in Slurry Bubble Column Reactor Without Liquid Circulation Methanol Production and H2/CO Mole Ratio in Liquid Phase due to Water Feed Effect in Slurry Bubble Column Reactor Without Liquid Circulation Methanol Production for Five Different Catalyst Sizes Obtained from Slurry Bubble Column Reactor Without Liquid Circulation

DESIGN OF SLURRY BUBBLE COLUMN REACTORS: NOVEL TECHNIQUE FOR OPTIMUM CATALYST SIZE SELECTION CONTRACTUAL ORIGIN OF THE INVENTION

CONTRACTUAL ORIGIN OF THE INVENTION

The United States Government has rights in this invention pursuant to the employer/employee relationship between the United States Government, represented by the Department of Energy, and the inventors.

FIELD OF THE INVENTION

This invention relates generally to fluidized bed reactors such as slurry bubble column reactors (SBCR) used for converting synthesis gas into liquid fuels and is particularly directed to the determination of optimum particle size for a catalyst in this type of reactor taking into consideration complete granular temperature balance based on the kinetic theory of granular flow as well as the effect of the volumetric mass transfer coefficient between the liquid and gas phases and the water gas shift reaction for optimum liquid fuel production.

BACKGROUND OF THE INVENTION

Major oil companies are gearing up to build slurry bubble column reactors (SBCR) to utilize natural gas located in remote areas of the world and to convert it to paraffin wax which will be upgraded to gasoline and Diesel fuels. SBCRs have recently become competitive with traditional fixed bed reactors for converting synthesis gas into liquid fuels. The advantages of the slurry-phase reactor over the fixed bed reactor are well documented. In slurry bubble column reactors, fine powdered catalysts are suspended in the fluid and gas bubbles provide the energy to keep the catalyst mixed. SBCRs have excellent heat and mass transfer characteristics for removal of the heat given off by exothermic reactions and the ability to replace catalyst easily.

The design and scale-up of SBCRs require, among other things, precise knowledge of kinetics, hydrodynamics and mass transfer characteristics over a wide range of operating conditions for reactors with a diameter as large as 7 m and a height of 30 m being built by the oil industry. Models applied to the F-T conversion of synthesis gas in a SBCR require hold-up correlations, diffusivity, mass transfer coefficients and bubble size as inputs. As an input in such a model, eddy diffusivities are measured using computer-aided radioactive particle tracking (CARPT) and mass transfer coefficients in three-phase flows, including fine particles. Hold-up profiles for these reactions have been measured, but coherent flow structures in bubble column reactors in the churn-turbulent regime have not been computed.

Computational fluid dynamics (CFD) is a recently developed tool which can help in the scale up. These multiphase CFD codes with viscosity as an input allow for the computation of hold-up and flow patterns for gas-liquid flow and gas-liquid-solids flow. Based on a kinetic theory model, the hold-up, flow patterns and methanol production in an Air Products/Department of Energy (DOE) Laporte slurry bubble column reactor have been computed and used for modeling new reactor designs. But most modeling studies have not addressed the effect of catalyst size on the performance of the reactor.

An issue of interest to the energy industry is the size of the catalyst used in slurry bubble column reactors. The industry is gearing up to make catalysts for slurry bubble column reactors. Fischer-Tropsch catalysts, such as those used to produce methanol and other liquids from synthesis gas normally are in powder form. Catalyst particles used in most fluidized bed processes are small enough such that external mass transfer and internal diffusion resistance are negligible. The size of the catalyst is typically in the range of 20 μm to 120 μm, although some workers in this area describe the preferred particle size as between 20 and 80 μm. Small particle sizes are needed to carry out the reaction. However, small particles become entrained in the product gas stream and are known to cause liquid product filtration problems. Small particles also cause the formation of the clusters, which give rise to large effective particle sizes and hence poor mass transfer.

The present invention is concerned with optimum particle size, which is the size that provides maximum granular temperature, similar to the experiments for gas-solid systems done at EXXON by Cody in 1996. For this particle size, the heat and the mass transfer coefficients have the highest values. In the present invention the mass transfer coefficient is an input and the mass transfer coefficient is correlated to the fluctuating velocities (granular temperature) as determined by a hydrodynamic model.

BRIEF DESCRIPTION OF THE DRAWINGS

The patent or application file contains at least one drawing executed in color. Copies of this patent with color drawing(s) will be provided by the Patent and Trademark Office upon request and payment of the necessary fee. The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

FIG. 7 illustrates the initial and boundary conditions for methanol synthesis;

DETAILED DESCRIPTION OF THE PREFERRED EMBODIMENTS

Figure 1:
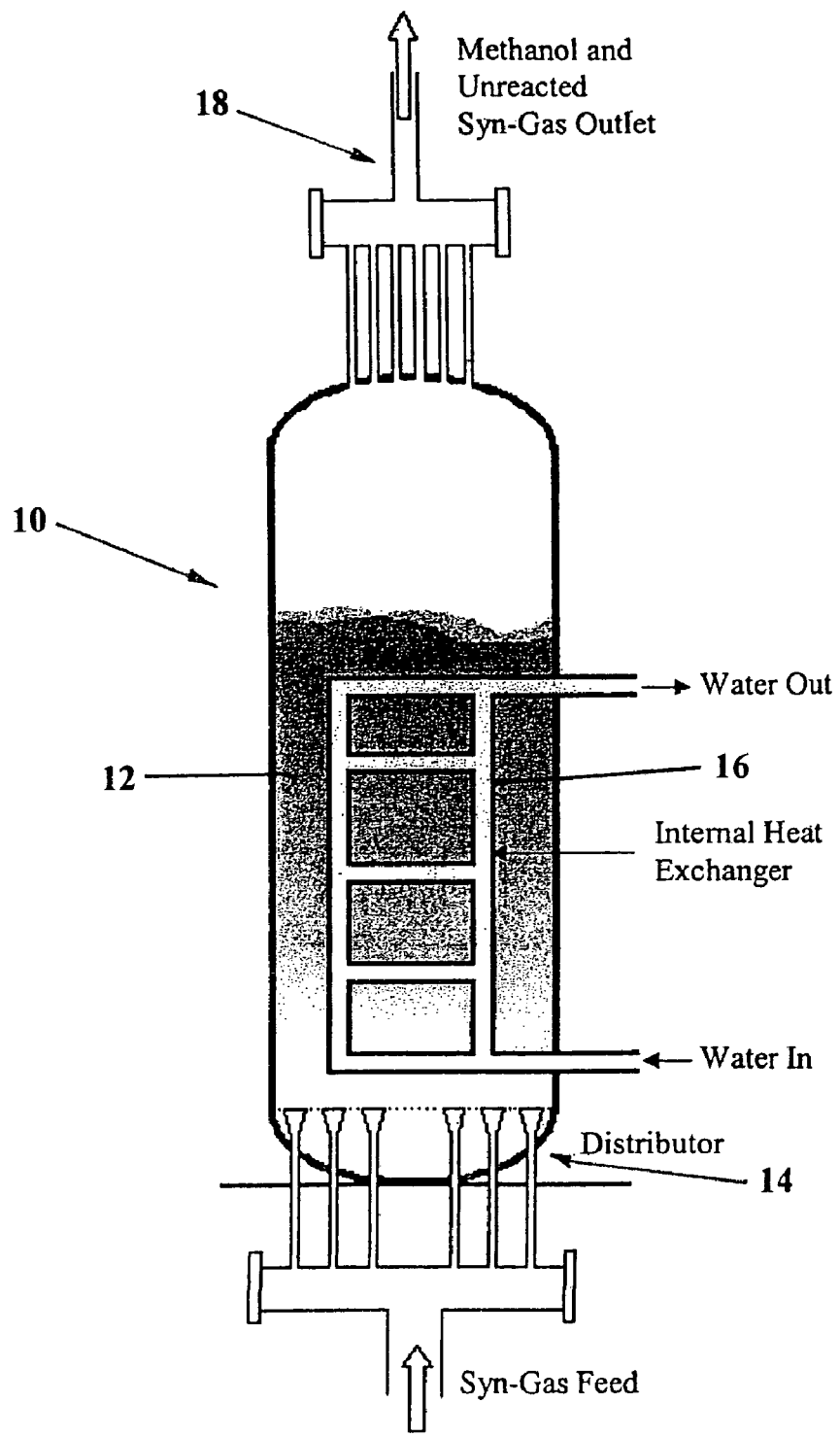
FIG. 1 is a simplified schematic illustration of the Air Products/Department of Energy (DOE) Laporte slurry bubble column reactor used in a liquid-phase methanol synthesis process.

A hydrodynamic model for the production of methanol from syn-gas in the slurry bubble column reactor was developed. It uses the principles of mass, momentum and energy conservation for each phase, as described in Table 1. This model includes the complete granular temperature balance based on the kinetic theory of granular flow. The kinetic theory model and the computer code were extended to include the effect of the mass transfer coefficient between the liquid and the gas and the water gas shift reaction in the Air Products/DOE Laporte slurry bubble column reactor shown in FIG. 1. The reaction rates for methanol are all in the gas phase in previous work. Here the more realistic rate in the liquid phase is used.

The following chemical reactions occur during production of methanol from syn-gas. The reactions included are methanol production from hydrogen and CO, the water gas shift reaction, and the production of methanol from $CO_2$-hydrogenation.

$$CO + 2H_2 \leftrightarrow CH_3OH$$

$$CO_2 + H_2 \leftrightarrow CO + H_2O \tag{1}$$

$$CO_2 + 3H_2 \leftrightarrow CH_3OH + H_2O$$

Graaf et al. developed the reaction rate for methanol synthesis in gas-catalyst phases and extended it to three phase methanol synthesis using gas-liquid solubilities in thermodynamical equilibrium described by Henry's law. The reactions of jxth species of the liquid phase are $$r_l^{jx} = \sum_{i=1}^{IX} \alpha_i^{jx} M^{jx} r_i' \tag{2}$$

The rates for the three reactions (IX=3) in the liquid phase are given as follows:

$$r_{IX}' = \frac{\varepsilon_s \rho_s}{1.0 \times 10^3} \cdot r_{IX}'' \left( \frac{\text{mol}}{\text{cm}^3 \cdot \text{sec}} \right) \tag{3}$$

where, $\alpha_i^{jx}$ represents the stoichiometric coefficient of jxth species in the ith reaction of liquid phase and $M^{jx}$ represents the molecular weight of jxth species. $r''_{IX}$ (mol/Kgcat·s) is the rate of reaction on catalyst surface for three reactions.

$$r''_{CH3OH,A3} = \frac{k^*_{ps,A3} k^*_{CO}(C_{CO} C_{H2}^{3/2} - C_{CH3OH}/(C_{H2}^{1/2} K_{C1}))}{(1 + k^*_{CO} C_{CO} + k^*_{CO2} C_{CO2})(C_{H2}^{1/2} + (k^*_{H2O}/k^{*1/2}_{H2}) C_{H2O})} \tag{4}$$

$$r''_{H2O,B2} = \tag{5}$$

$$\frac{k^*_{ps,B2} k^*_{CO2}(C_{CO2} C_{H2} - C_{H2O} C_{CO}/K_{C2})}{(1 + k^*_{CO} C_{CO} + k^*_{CO2} C_{CO2})(C_{H2}^{1/2} + (k^*_{H2O}/k^{*1/2}_{H2}) C_{H2O})} = r''_{co,B2}$$

$$r''_{CH3OH,C3} = \tag{6}$$

$$\frac{k^*_{ps,C3} k^*_{CO2}(C_{CO2} C_{H2}^{3/2} - C_{CH3OH} C_{H2O}/(C_{H2}^{3/2} K_{C3}))}{(1 + k^*_{CO} C_{CO} + k^*_{CO2} C_{CO2})(C_{H2}^{1/2} + (k^*_{H2O}/k^{*1/2}_{H2}) C_{H2O})} = r''_{H2O,C3}$$

where, chemical equilibrium constants are $$K_{C1} = 1.72 \times 10^{-16} e^{\left(\frac{126011}{RT}\right)}, \tag{7}$$

$$K_{C2} = 5.81 \times 10 e^{\left(\frac{-33760}{RT}\right)}, K_{C3} = K_{C1} \times K_{C2}$$

Reaction rate constants are $$k^*_{ps,A3} = 1.66 \times 10^5 e^{\left(\frac{-93925}{RT}\right)}, k^*_{ps,B2} = 7.21 \times 10^{17} e^{\left(\frac{-215130}{RT}\right)} \tag{8}$$

$$k^*_{ps,C3} = 8.52 \times 10^{-1} e^{\left(\frac{-43425}{RT}\right)}, k^*_{CO} = 9.01 \times 10^{-12} e^{\left(\frac{92138}{RT}\right)}$$

$$k^*_{CO2} = 3.15 \times 10^{-5} e^{\left(\frac{34053}{RT}\right)}, k^*_{H2O}/k^{*1/2}_{H2} = 2.71 \times 10^{-12} e^{\left(\frac{103030}{RT}\right)}$$

$C_{jx}$ (mol/m$^3$) is the bulk concentration of the jxth species in the liquid phase and R is the gas constant of 8.314 (J/mol-K).

The rate of mass transfer for each phase (k) is $$\dot{m}_k = \sum_{jx=1}^{n} \dot{m}_k^{jx} M^{jx} \tag{9}$$

Only mass transfer between the gas phase and the liquid phase was considered in developing this invention.

$$\dot{m}_l = \sum_{jx=1}^{n} \dot{m}_l^{jx} M^{jx} = -\dot{m}_g, \dot{m}_s = 0 \tag{10}$$

Mass transfer rate between gas phase and liquid phase can be expressed in terms of the volumetric mass transfer coefficient and the concentration difference between gas-liquid interface phase and liquid phase.

$$\dot{m}_l^{jx} = \varepsilon_l k_l a \left( C_{jx}^{g-l} - C_{jx} \right) \times \frac{1}{10^6} \left( \frac{mol}{cm^3 \cdot sec} \right) \tag{11}$$

where, $k_l a$ ($s^{-1}$) is the volumetric mass transfer coefficient and $C^{g-l}_{jx}$ is the concentration of the jxth species at gas-liquid interface phase which can be defined by Henry's law. The fugacity of a very dilute species in a liquid phase is linearly proportional to its mole fraction at low mole fractions.

$$f_{jx} = H_{jx} C^{g-l}_{jx} (mol/m^3) \tag{12}$$

In gas-liquid phase equilibrium, the fugacity of liquid phase can be the fugacity of gas phase defined by partial pressure of species in the gas phase.

$$f_{jx} = y'_{jx} P (bar) \tag{13}$$

where, $f_{jx}$ (bar) is the fugacity of the jxth species, $y'_{jx}$ is the mole fraction of jxth species and $H_{jx}$ (bar·m³/mol) is the Henry's constant of the jxth species used.

$$H_{CO} = 0.175 e^{\left(\frac{638}{RT}\right)}, H_{CO2} = 0.402 e^{\left(\frac{-6947}{RT}\right)}, H_{H2} = 0.0782 e^{\left(\frac{4875}{RT}\right)} \tag{14}$$

$$H_{H2O} = 0.330 e^{\left(\frac{-8633}{RT}\right)}, H_{CH3OH} = 1.49 e^{\left(\frac{-17235}{RT}\right)}$$

Figure 2:
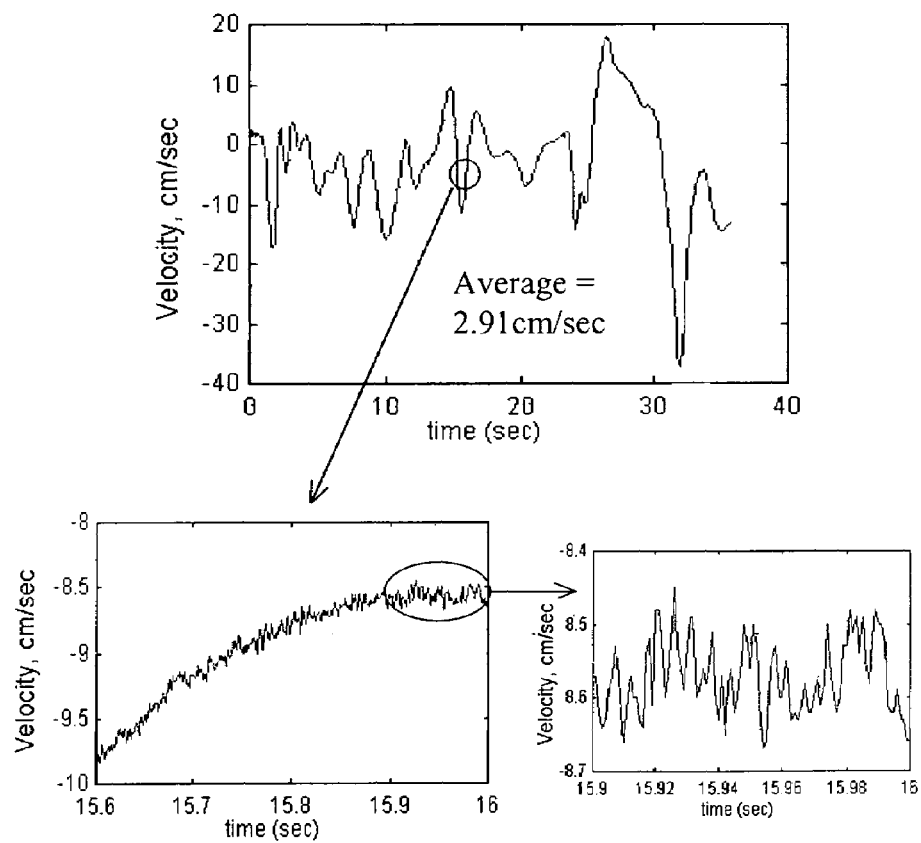
FIG. 2 is a graphic illustration of large- and small-scale oscillations in axial velocity of a solid as a function of time at x=15.5 cm and y=11.5 cm of the two-dimensional velocity input model used in the present invention.

The computer simulations of the IIT slurry bubble column (30.48 cm×5.08 cm×213.36 cm) were conducted. Water was recirculated through the bed, air was injected through porous tubes. The particles were 800 μm leaded glass beads with a density of 2.94 g/cm³. Many small bubbles act like another set of particles under the condition for $U_g$=3.37 cm/s and $U_l$=2.02 cm/s in the system. FIG. 2 shows typical large and small scales oscillations of particles obtained with the grid size of 1 cm. We computed the average random kinetic energy from such data. This gives us a granular temperature-like quantity. The granular temperature, ⅔ turbulence kinetic energy, can be introduced as a function of the particle fluctuation velocity. Here we have varied the particle sizes from 120 down to 20 μm and discovered a maximum in the granular temperature shown in FIG. 3. The computed granular temperature is about 202 (cm/s)² for 20 μm. It rises to 356 (cm/s)² for 60 μm, and then decreases to 138 (cm/s)² for 100 μm. The maximum granular-like temperature is at 60 μm, with a solid loading of about 10%. Geldart A glass spheres exhibit an order magnitude higher granular temperature than neighboring Geldart B glass spheres based on experiments in a gas-solid bubbling bed. A maximum for the gas-solid system is about 34 (cm/s)² at a particle size of about 75 μm. Our computed value of the granular-like temperature is almost an order of magnitude higher due to the fact that we have a flowing liquid stream. In the absence of liquid flow, our previous computations gave us a granular temperature of about 20 (cm/s)². The turbulent kinetic energy for gas-liquid flow measured with a radioactive particle tracer was as high as 2000 (cm/s)². This high value of turbulence is probably due to the fact that the actual gas velocity in the bubble column is an order of magnitude higher. An approximate relationship between the granular temperature and the particle velocity from the kinetic theory analysis is as follows:

$$\frac{\sqrt{\theta}}{v_s} = 0.5 \tag{15}$$

where θ is the maximum granular temperature in the system and $v_s$ is the average particle velocity in the upstream portion of the fluidized bed column.

The relationship between the granular temperature and the mass transfer coefficient in the slurry bubble column reactor can be obtained as follows. In the fluidized bed, the catalyst particles have random and deterministic velocity components. Fluidized bed dynamics for such systems without an input for mass transfer coefficient is beyond the present state-of-the art of the present CFD computations. To date, workers in this area have only been able to predict the bed expansion in such systems using solutions of the Navier-Stokes equations for the fluid and letting the particles oscillate. The computations with mass transfer will require resolution of very thin boundary layers. Hence such computations are beyond state-of-the art computers. Instead, we have carried out an order of magnitude analysis to relate the mass transfer coefficient to the granular temperature.

Figure 4:
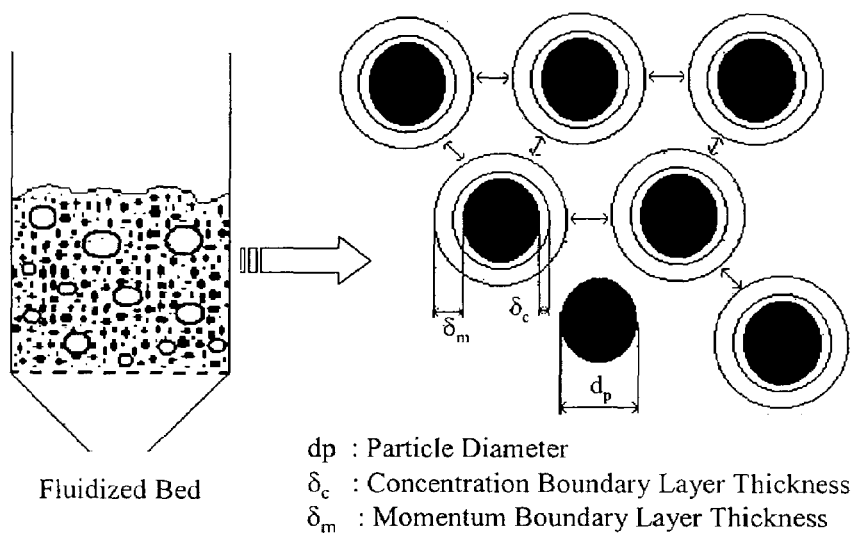
FIG. 4 illustrates the concentration and momentum boundary layers for particles in a slurry column bubble reactor, where it is assumed that a liquid layer surrounds the particles.

By definition the mass transfer coefficient ($k_L$) is related to the diffusivity ($D_L$) of gas in liquid and the concentration boundary layer thickness ($\delta_c$) shown in FIG. 4, as follows:

$$k_L = \frac{D_L}{\delta_c} \tag{16}$$

The momentum boundary layer thickness ($\delta_m$) can be related to the characteristic velocity, square root granular temperature ($\sqrt{\theta}$) and the characteristic length, and the particle diameter ($d_p$) by the following relationship:

$$\delta_m = \sqrt{\frac{v d_p}{\sqrt{\theta}}} \tag{17}$$

where, v is the kinematic viscosity.

The concentration boundary layer thickness is related to the momentum boundary layer thickness through the Schmidt number (Sc=v/$D_L$) as follows:

$$\delta_c = \frac{1}{Sc^{\frac{1}{3}}} \delta_m \tag{18}$$

Substitution yields the following relationship between the mass transfer coefficient and the granular temperature.

$$k_L = \frac{D_L \sqrt[4]{\theta}}{\sqrt{v d_p}} Sc^{\frac{1}{3}} \tag{19}$$

Figure 3:
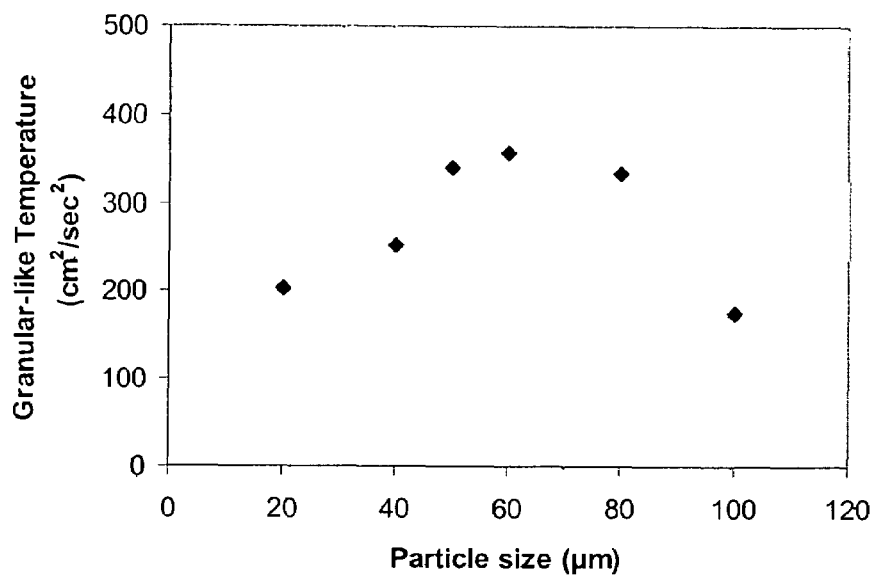
FIG. 3 is graphic illustration of the optimum particle size for mixing (maximum granular-like temperature) in the slurry bubble column located at Illinois Institute of Technology in Chicago, Ill., where $V_L$=2.02 cm/s and $V_G$=3.37 cm/s.

Equation (19) shows how the mass transfer coefficient can be deduced from the computed granular temperature. Substitution for the optimum particle size of 60 μm in the graph of FIG. 3 gives a reasonable value for mass transfer coefficients compared to literature values and rate constants for the reaction. The mass transfer limitation for 60 μm will be negligible for the slurry bubble column reactor with liquid recirculation. The mass transfer limitation without liquid recirculation will probably be small, but not negligible.

Figure 5:
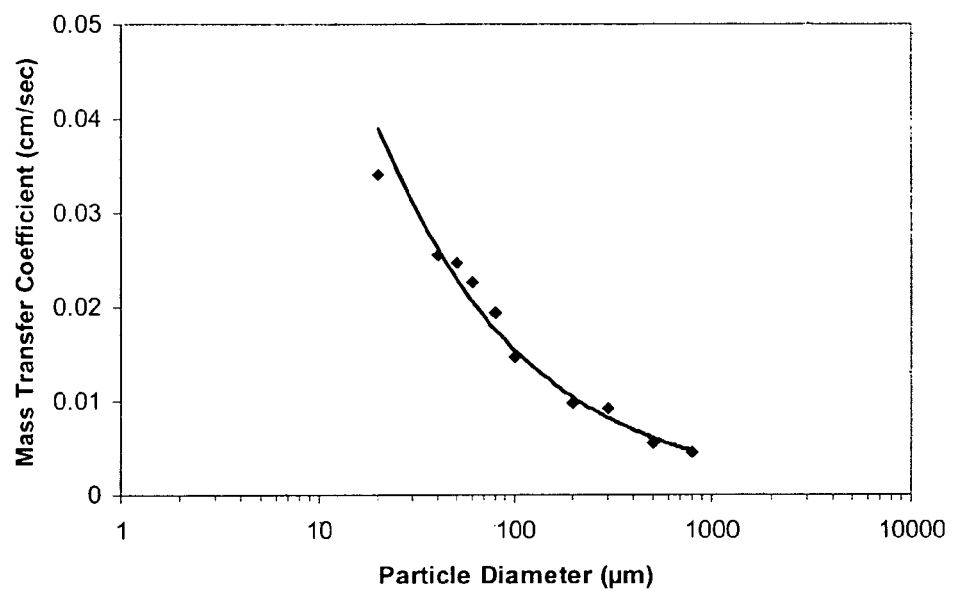
FIG. 5 graphically illustrates the variation of the mass-transfer coefficient with particle diameter as measured in microns for the particle sizes and granular-like temperatures shown in FIG. 3.

FIG. 5 shows the mass transfer coefficient obtained from the computed granular temperatures of FIG. 3. The mass transfer coefficient generally increases with decrease of particle diameter. As catalyst size is decreased, the combined resistance to internal diffusion, reaction, and external diffusion will be negligible. As a result, the absorption from the gas phase into the liquid phase will be the main resistance. The catalyst concentration should increase for the higher production rate. The process of coagulation due to random motion and subsequent collision of particles may be considered in the slurry bubble column reactor.

The effective particle diameter is obtained from coagulation theory as $$d_e(t) = d_0(1+N_0Kt)^{1/3} \quad (20)$$

where, $d_e$ is the particle size at time t, $d_0$ is the initial particle size, $N_0$ is the particle concentration and K is the coagulation coefficient.

The solid volume fractions for Geldart A particles were a constant value of about 10% from the simulation. The particle concentrations were estimated from the particle diameters with the solid volume fraction of 10%. As a rule of thumb, if the particle concentration is less than $10^6/cm^3$, for particles larger than 120 μm in our simulation, the coagulation of particles is neglected. Time (t) was determined by such a principle. There is no coagulation for particles larger than 120 μm. The coagulation coefficients were calculated for particles at standard conditions. The effective particle diameters calculated from the coagulation theory. The volumetric mass transfer coefficient based on an effective particle diameter is given as $$k_L \cdot a = \frac{D_L \sqrt[4]{\theta}}{\sqrt{vd_e}} Sc^{\frac{1}{3}} \cdot \frac{6}{d_e} \varepsilon_s \quad (21)$$

where, $D_L$ is the diffusivity of $10^{-5}$ cm²/s and a is the interfacial area per unit volume estimated from the effective particle diameter.

Figure 6:
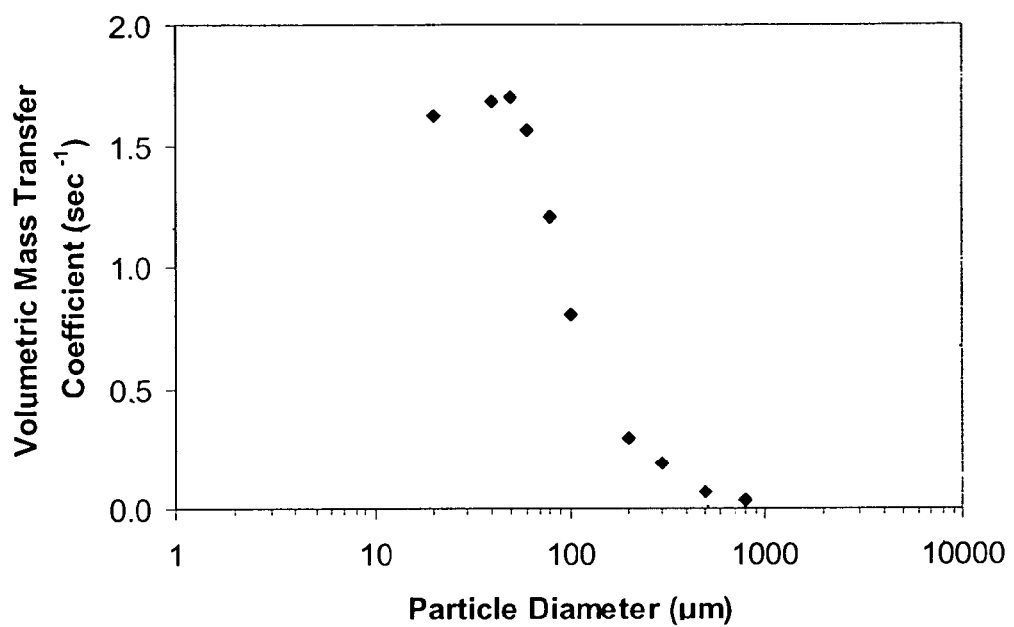
FIG. 6 is a graphic illustration of the variation of the volumetric mass-transfer coefficient with the effective particle diameter measured in microns using the coagulation theory.

The volumetric mass transfer coefficient based on an effective particle diameter has a maximum value near a particle diameter of 50 μm as shown in FIG. 6. It may be larger than the estimated value due to non-spherical particle effects or electrical forces. As pointed out previously, small particles cause the formation of clusters, which give rise to large effective particle sizes and hence poor mass transfer. Large particles, Geldart B particles, have very low mass transfer coefficients and hence poor production rate.

A search for an optimum catalyst size was carried out for methanol synthesis in the DOE Laporte slurry bubble column reactor 10 shown in FIG. 1. A powdered catalyst is suspended in an inert liquid 12 to form a slurry, and feed gas is introduced into the bottom of the reactor 10 through a distributor 14. The upward flowing gas bubbles provide the energy to keep the slurry highly mixed. The reactants from the gas phase dissolve in the liquid and diffuse to the catalyst surface, where they react. Heat is removed by generating steam in an internal tubular heat exchanger 16. Methanol and unreacted syn-gas is removed via an outlet 18 located on an upper portion of the reactor 10.

The initial conditions and the configuration for the simulation are shown in FIG. 7. To obtain the numerical solution of nonlinear-coupled partial differential equations, the IIT-NETL code was used. Simulations using the granular temperature model were carried out in two-dimensional Cartesian coordinates with a total of 34×160 computational meshes. The Johnson and Jackson slip boundary condition described in Table 1 was employed for the solid phase. Neumann boundary conditions were applied to the three-phase flow with a constant pressure of 753.2 psig at the top wall. The boundary conditions at the bottom wall were that the axial gas velocity is a parabolic profile with an average velocity of a 15.24 cm/s, with zero velocity near the wall. Solids and liquid velocities are zero at the bottom wall.

The restitution coefficient due to particle-particle collisions was 0.9995 for the simulation. The measurement of radial distribution functions of statistical mechanics showed that particles fluidized in water fly apart well before contact, at a radius of about 50% larger than the particle radius. In liquids there exists a film between the particles that gives rise to a lubrication force. Thus, the restitution coefficient can be close to unity. The total volumetric mass transfer coefficient was 0.5 s$^{-1}$ for the reference condition. The syn-gas composition fed into the bottom of the reactor is shown in Table 2. In the initial condition of the simulation, the syn-gas composition in the reactor was only Nitrogen. The convergence criterion for the simulation was $10^{-4}$. The simulations were run for 40 seconds and then averaged from 15 to 30 s.

A search for an optimum catalyst size was carried out for methanol synthesis in the DOE Laporte slurry bubble column reactor using the kinetic theory model of granular flow. This model included the effect of the mass transfer coefficient between the liquid phase and the gas phase and the water-gas shift reaction.

Figure 8:
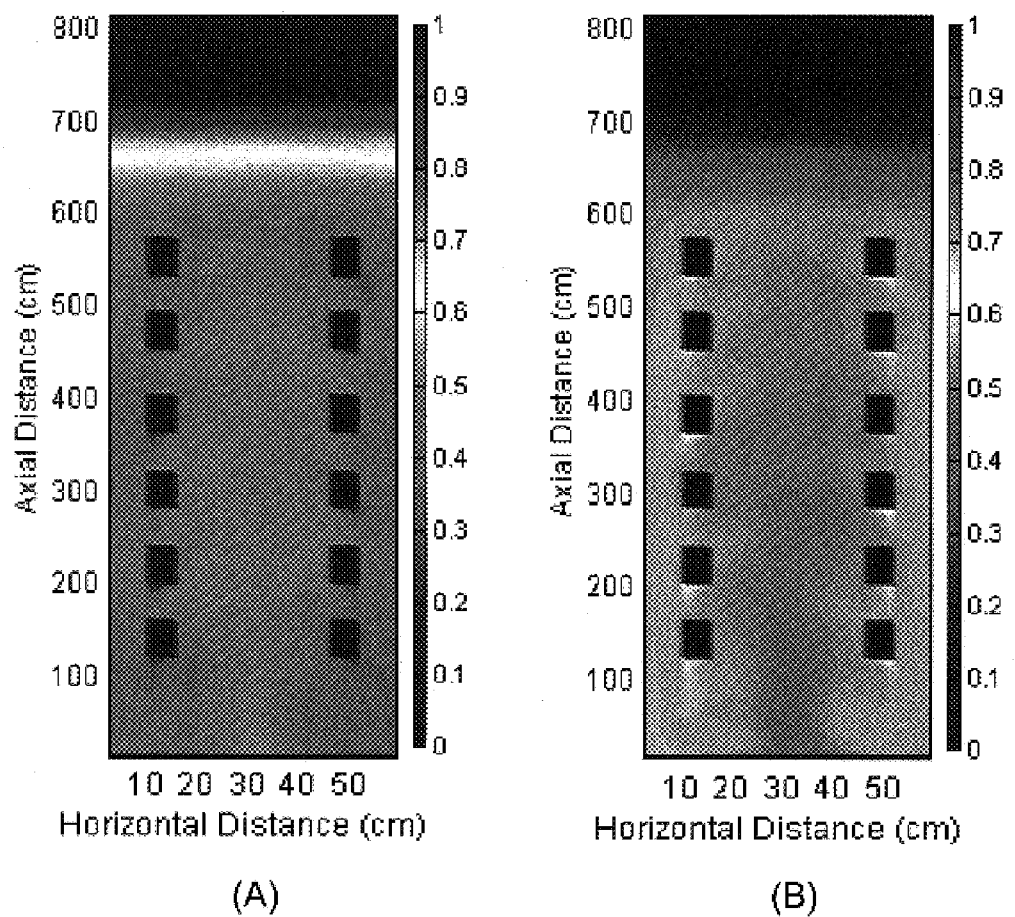
FIG. 8 illustrates the computed gas (A) and liquid (B) holdup averaged from 15 to 30 s in the simulation of methanol synthesis as carried out at the Air Products/DOE SBCR using the kinetic theory. The color bar shows the range of gas and liquid volume fractions.
Figure 9:
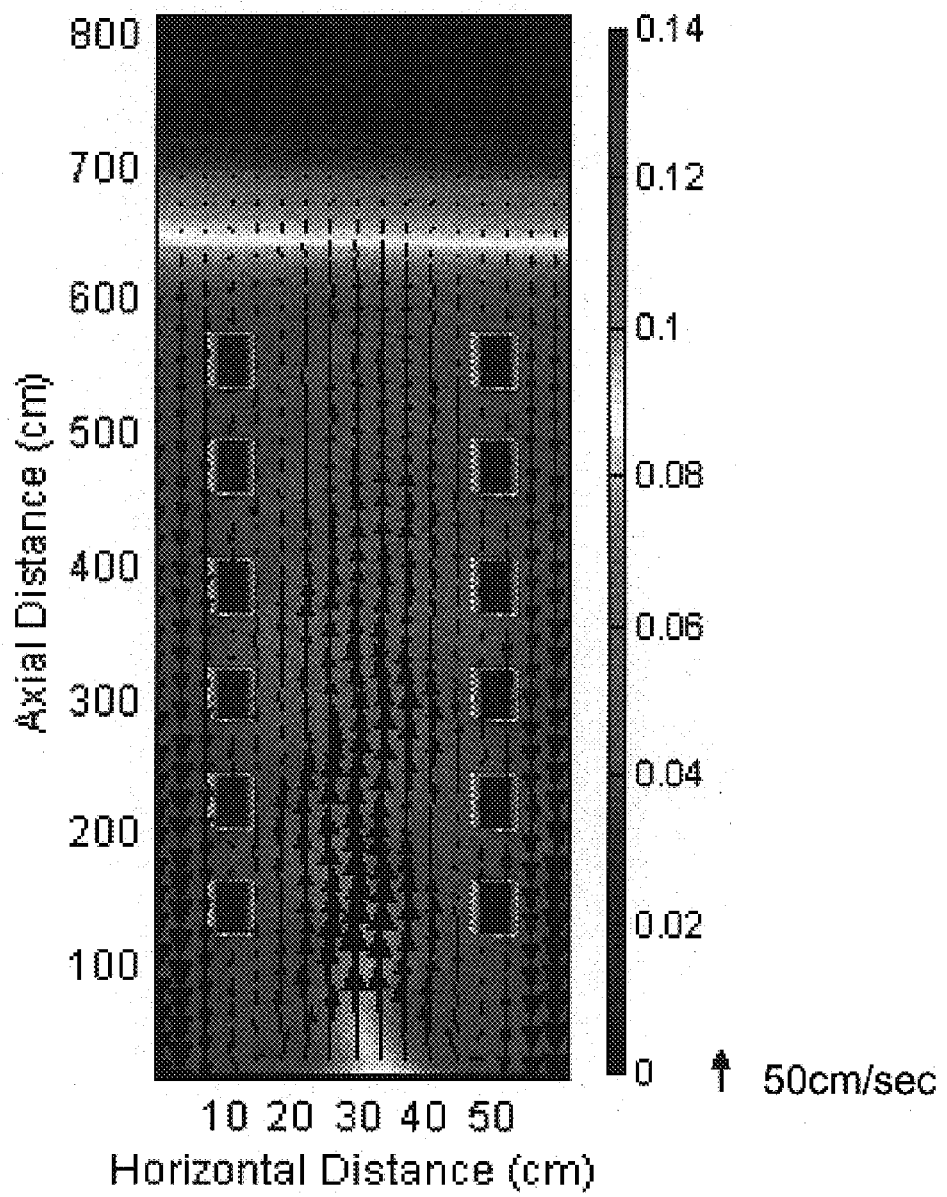
FIG. 9 illustrates the computed catalyst volume fraction and catalyst flow pattern averaged from 15 to 30 s in the simulation of methanol synthesis using the kinetic theory in the Air Products/DOE SBCR.
Figure 10:
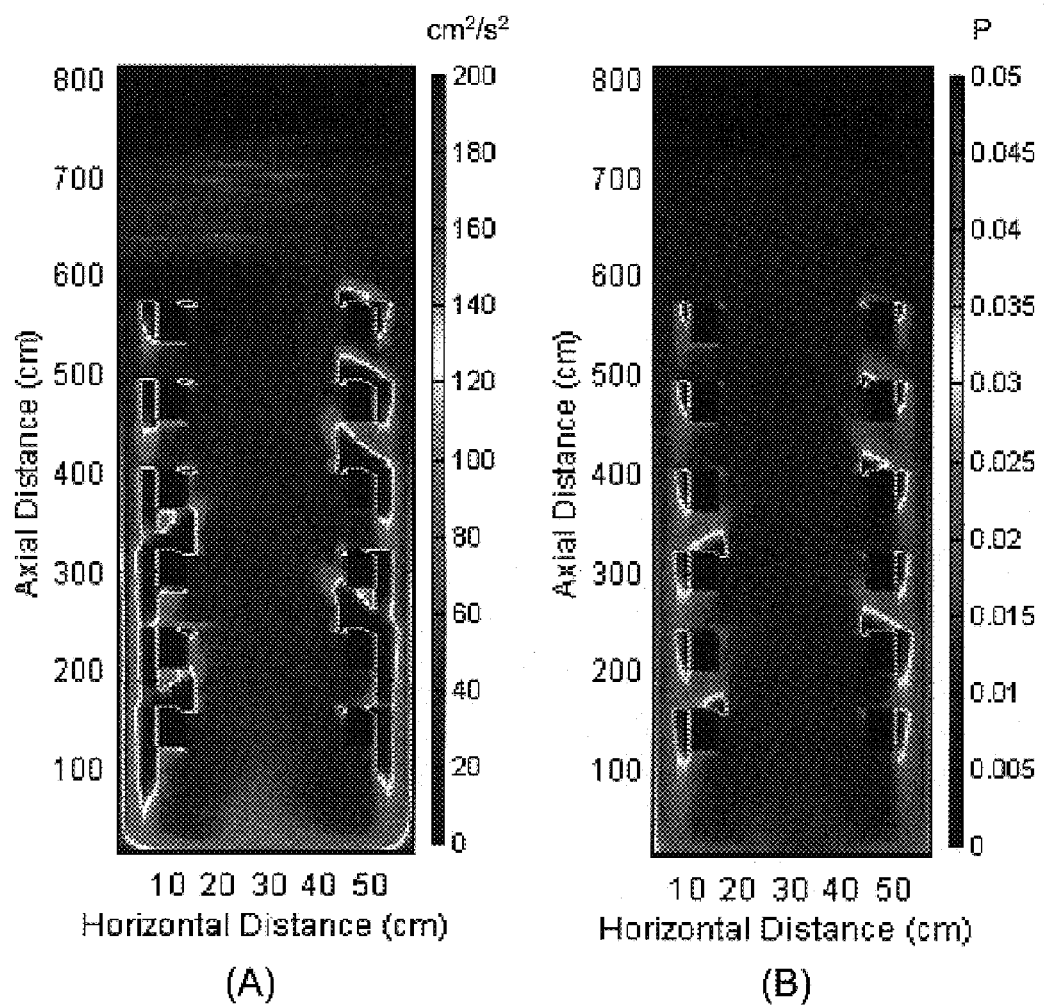
FIG. 10 graphically illustrates the granular temperature in cm2/s2 (A) and catalyst shear viscosity in poises (B) averaged from 15 to 30 s in the simulation of methanol synthesis using the kinetic theory for the Air Products/DOE SBCR.

FIGS. 8, 9 and 10 show the computed liquid and gas hold-ups, the flow patterns, the granular temperature, and the slurry viscosity averaged from 15 to 30 s for Laporte's methanol synthesis. The computed average gas volume fraction is approximately 0.35. As expected, it is higher at the center of the reactor. The average liquid volume fraction is approximately 0.52 and the average catalyst volume fraction is approximately 0.13. The basic computed flow pattern is upflow in the center and downflow at the wall as observed in the pilot plant. There are however many additional vortices around the heat exchanger tubes not shown in FIG. 9 due to time averaging. The average computed granular temperature is approximately 30 cm²/s. The average computed catalyst viscosity is close to 1 cp. It is much higher around the heat exchanger tubes due to the higher granular temperature at this location. The new effect is due to the use of a more realistic Johnson-Jackson boundary conditions. Hence, there may be higher corrosion or collisions near the heat exchanger.

Figure 11:
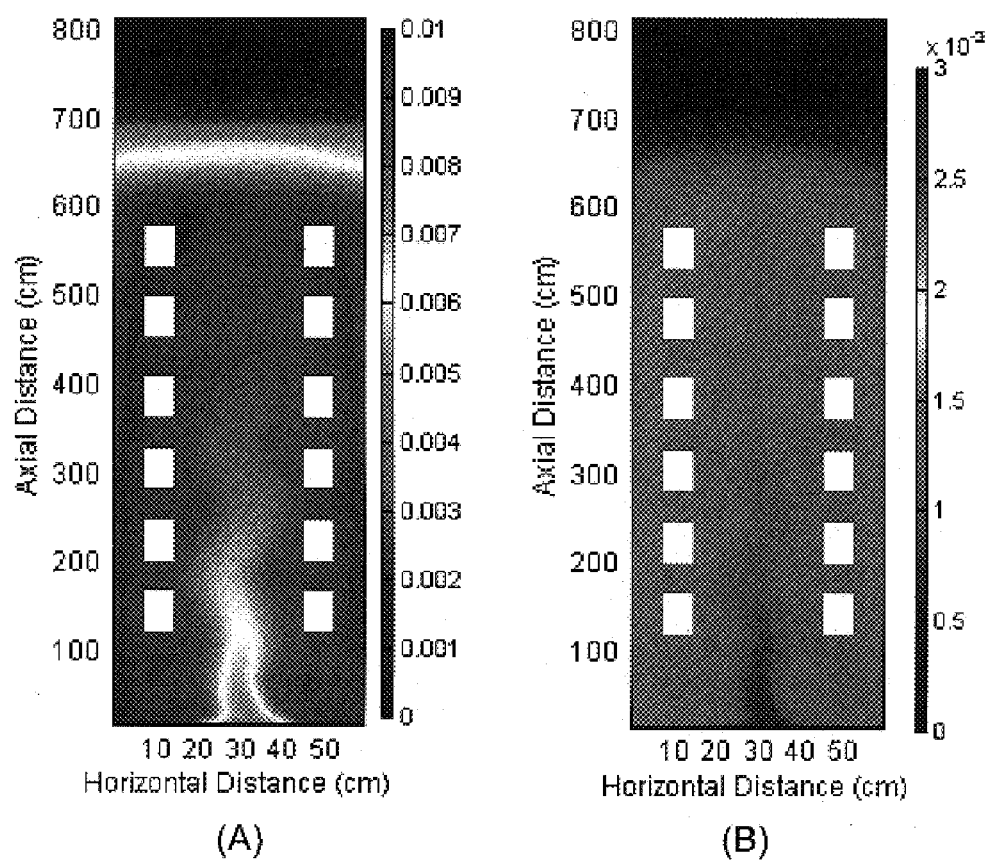
FIG. 11 is a graphic illustration of the computed mole fraction of methanol (A) and water (B) in the gas phase averaged from 15 to 30 s in the simulation of methanol synthesis using the kinetic theory for the Air Products/DOE SBCR.
Figure 12:
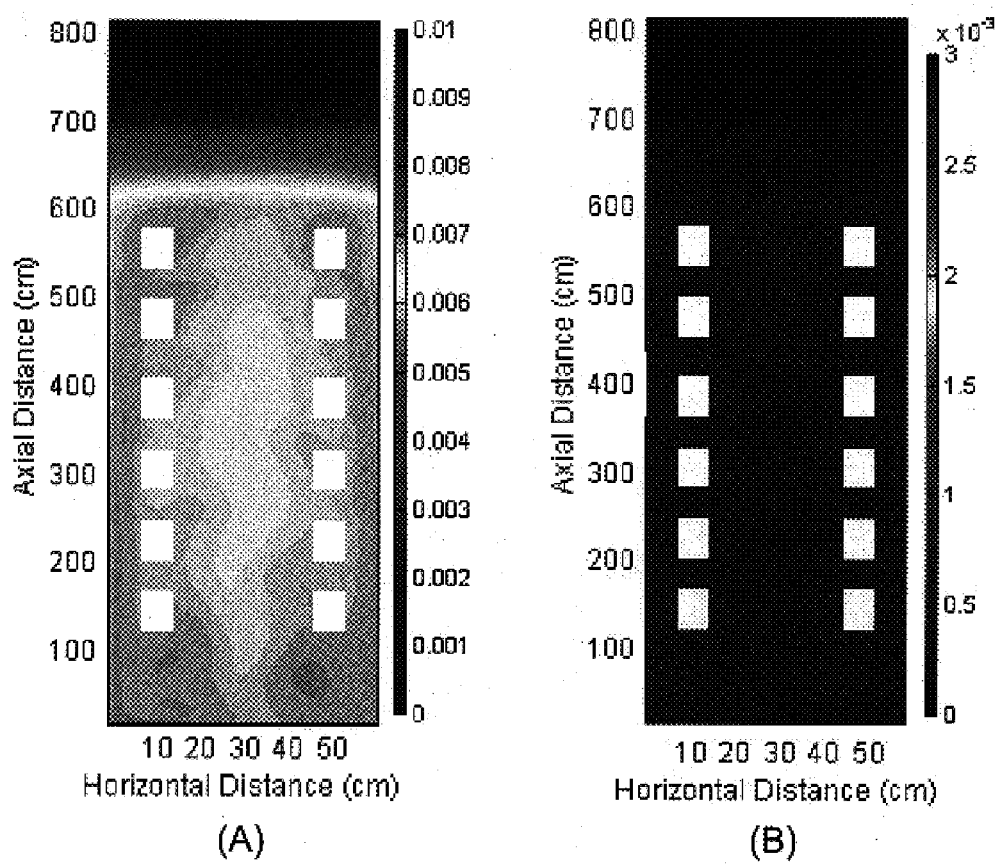
FIG. 12 graphically illustrates the computed mole fraction of methanol (A) and water (B) in the liquid phase averaged from 15 to 30 s in the simulation of methanol synthesis using the kinetic theory for the Air Products/DOE SBCR.

The mole fraction of methanol and water in the gas and the liquid phases are shown in FIGS. 11 and 12. The product water concentration is small, since we assumed the inlet synthesis gas was dry. FIGS. 11 and 12 show that the mixing in the reactor is very good. With the water gas shift reaction, the ratio of $H_2$ to CO is 0.5 due to chemical equilibrium in the liquid phase of the simulation.

Figure 13:
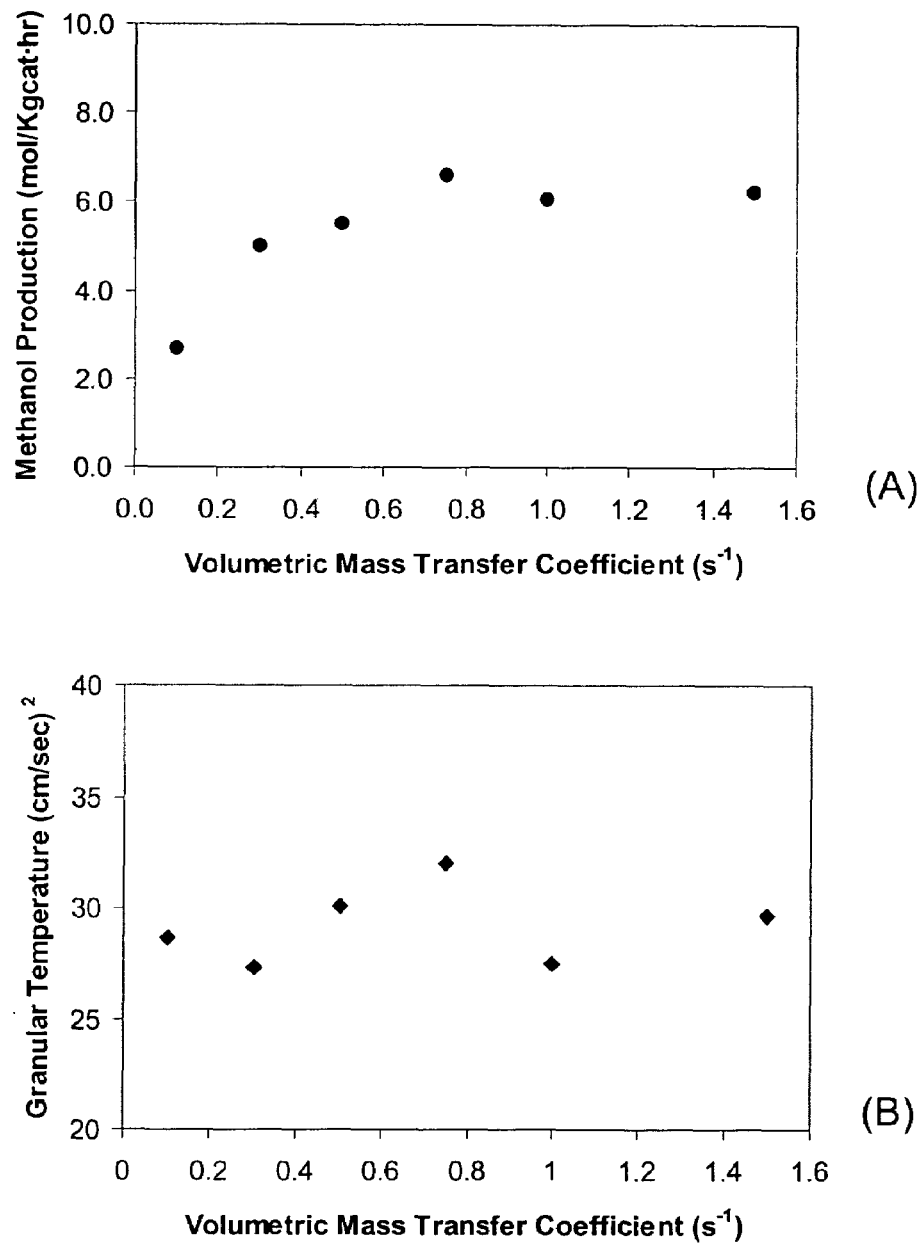
FIG. 13 graphically illustrates methanol production and granular temperature obtained from the different volumetric mass-transfer coefficients in the SBCR without liquid circulation.
Figure 14:
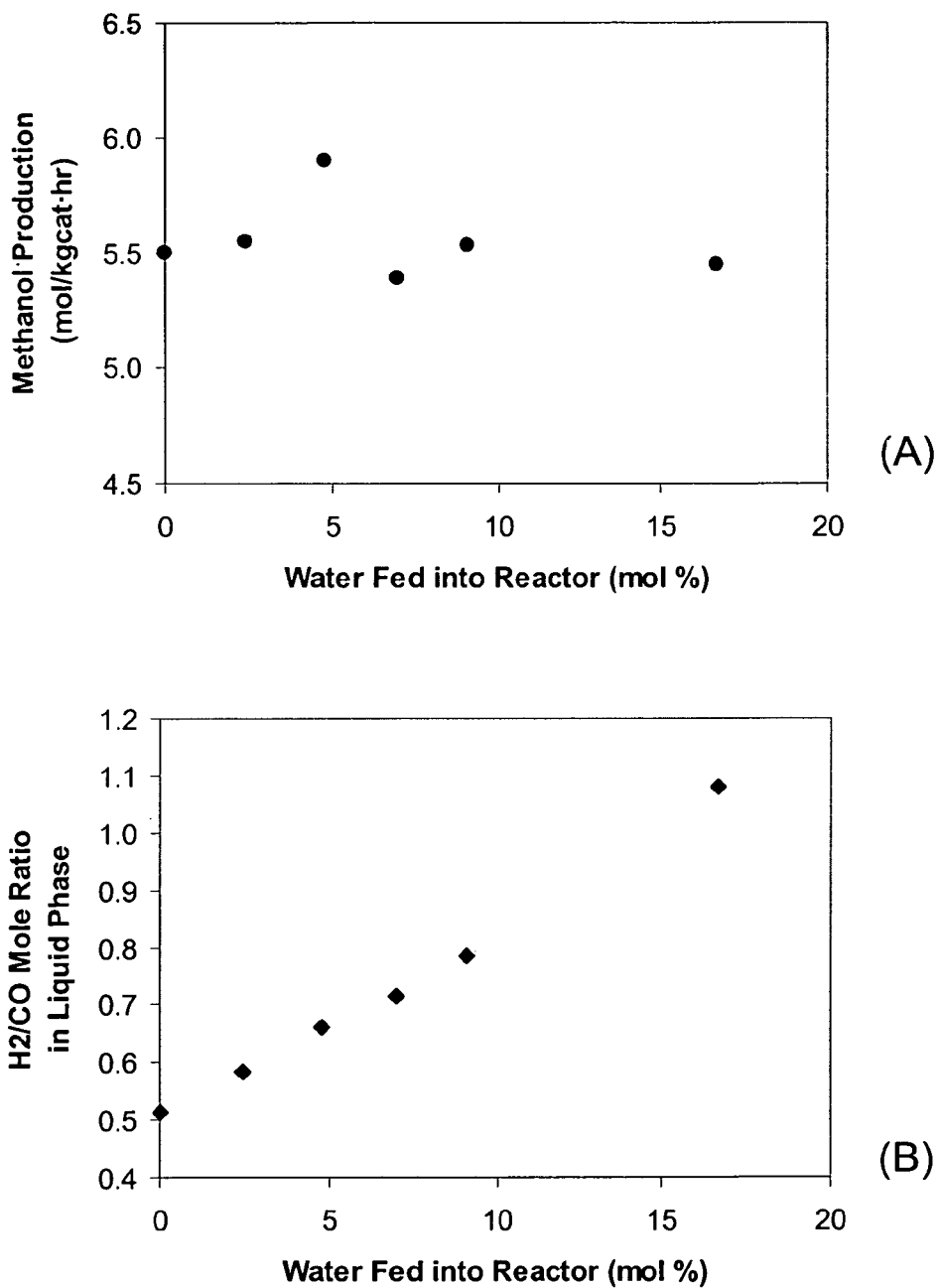
FIG. 14 graphically illustrates methanol production (A) and $H_2/CO$ mole ratio in the liquid phase (B) due to the water feed effect in the SBCR without liquid circulation.

FIG. 13 shows the effect of the volumetric mass transfer coefficient estimated by the simulation in slurry bubble column reactor without liquid circulation. Methanol production increases 6.5 mol/kgcat·hr for the volumetric mass transfer coefficient of 0.75 and then the methanol production is no longer limited by the volumetric mass transfer coefficient. In this region, the granular temperature is a maximum at 33 (cm/s)². This suggests that the maximum methanol production can be at the maximum granular temperature shown in FIG. 3. The estimated volumetric mass transfer coefficient is in good agreement with experimental values shown in the literature. FIG. 14 shows the effect of water in synthesis gas fed into the reactor. Methanol production is maximum at a water mole fraction of 0.05, and then decreases slowly with increasing water. Enhanced production due to the addition of water can be determined by a balance between the rates of water gas shift reaction and $CO_2$-hydrogenation as well as the composition of the synthesis gas fed into the reactor. However, the addition of large quantities of water decreases the rate of methanol production due to deactivation of the catalyst. Hence, the ratio of fresh gas to recycled gas in the slurry bubble column reactor can be set near the water mole fraction of 0.05. The ratio of $H_2$ and CO in the liquid phase increases linearly by adding the water due to chemical equilibrium.

Figure 15:
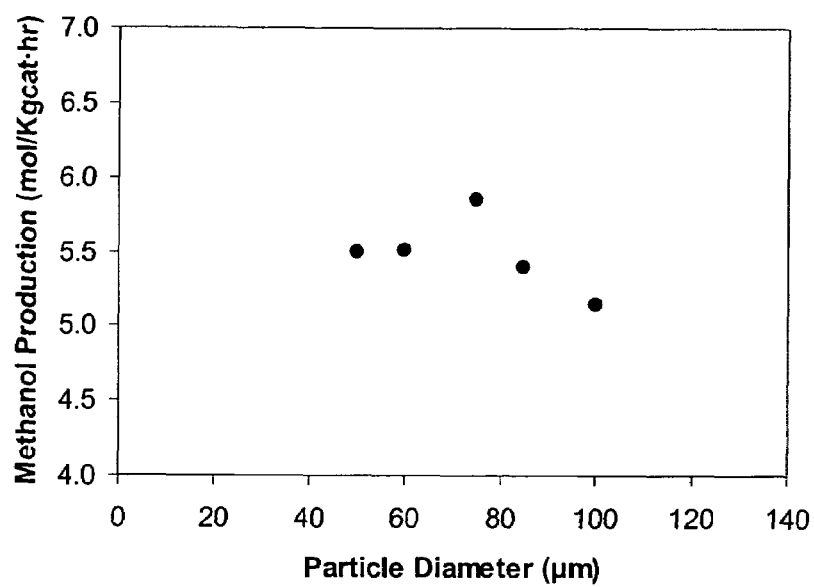
FIG. 15 is a graphic illustration of the methanol production for five different catalyst particle sizes obtained from the SBCR without liquid circulation.

FIG. 15 illustrates methanol production for five different catalyst sizes. For 75 microns, production is increased, then decreases substantially for 100 microns. Hence, the optimum particle size is about 70 microns. This agrees with the previous simulations of about 60 microns for the case of no reaction.

The use of slurry bubble column reactors (SBCRs) for the production of methanol and other hydrocarbons from synthesis gas is of great interest to the worldwide energy industry. Computational fluid dynamics (CFD) is a recently developed tool which can help in the scale up. A critical issue in SBCRs which has not been addressed in the literature is that of optimum catalyst particle size. The present invention permits determination of optimum catalyst particle size for fluidized bed reactors. The inventive method can be applied to gas-solid, liquid-solid, and gas-liquid-solid fluidized bed reactors, as well as to the Laporte slurry bubble column reactor. Computations carried out using the present invention show that there is a factor of approximately two difference between 20 and 60 µm particle size with maximum granular temperature (turbulent kinetic energy) near the 60 µm size particles in the production of methanol and other hydrocarbons.

The inventive method also permits accurate determination of the mass transfer coefficient in slurry bubble column reactors and other fluidized beds, as well as bubble columns where the catalyst particle is replaced by an effective droplet or by an oscillating small bubble in a bubble column. Prior kinetic theory models have been extended by this invention to include the effect of the mass transfer coefficient between the liquid and the gas and the water gas shift reaction in the slurry bubble column reactor. The computed granular temperature is approximately 30 $cm^2/s$ and the computed catalyst viscosity is approximately 1.0 cp. The volumetric mass transfer coefficient determined using the present invention is in good agreement with experimental values presented in the literature. The optimum particle size was determined for maximum methanol production in an SBCR. This size is approximately 60-70 microns, for the case of maximum granular temperature. This particle size is similar to the size of FCC particles used in petroleum refining.

While particular embodiments of the present invention have been shown and described, it will be obvious to those skilled in the relevant arts that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

| Notation | |
|---|---|
| a | interfacial area per unit volume |
| $C_d$ | drag coefficient |
| $C_{jx}$ | bulk concentration |
| $C_{jx}^{g-l}$ | concentration of the jxth species at gas-liquid interface phase |
| D | Diffusivity |
| $d_k$ | characteristic particulate phase diameter |
| e | coefficient of restitution |
| $f_{jx}$ | fugacity of the jxth species |
| g | Gravity |
| $g_o$ | radial distribution function |
| $H_{jx}$ | Henry's constant of the jxth species |
| K | mass transfer coefficient |
| K | coagulation coefficient |
| ka | volumetric mass transfer coefficient |
| k* | reaction rate constant |
| $k_c$ | chemical equilibrium constant |
| $M^{jx}$ | molecular weight of the jxth species |
| $m_k^{jx}$ | mass transfer rate of the jxth species in k phase |
| $N_0$ | particle concentration |
| P | continuous phase pressure |
| $P_k$ | dispersed(particulate) phase pressure |
| R | gas constant |
| $Re_k$ | Reynolds number for phase k |
| $r_{IX}'$ | reaction rate based on unit volume |
| $r_{IX}''$ | reaction rate based on weight of catalyst |
| Sc | Schmidt number |
| t | Time |
| T | Temperature |
| $U_{sl}$ | slip velocity |
| v | hydrodynamic velocity |
| $y_{jx}'$ | Gas mole fraction of the jxth species in k phase |

| Greek Letters | |
|---|---|
| $\alpha_i^{jk}$ | stoichiometric coefficient of the jxth species in the ith reaction |
| $\beta_B$ | interphase momentum transfer coefficient |
| $\delta_c$ | concentration boundary layer thickness |
| $\delta_m$ | momentum boundary layer thickness |
| $\epsilon_k$ | volume fraction of phase k |
| $\gamma_s$ | energy dissipation due to inelastic particle collision |
| $\kappa_s$ | granular conductivity |
| $\lambda_k$ | bulk viscosity of phase k |
| $\mu_k$ | shear viscosity of phase k |
| v | kinematic viscosity |
| $\ominus$ | granular temperature |
| $\rho_k$ | density of phase k |
| $\tau_k$ | stress of phase k |
| $\Phi$ | specularity coefficient |

| Superscripts | |
|---|---|
| jx | Species |
| * | Concentration-based kinetic parameters |

| Subscripts | |
|---|---|
| g, l, s | gas, liquid, solid respectively |
| jx | Species |
| k | Phases |
| ps | Pseudo |

TABLE 1

Hydrodynamic Kinetic Theory Model for Multiphase flow (k = l, g, s)

Continuity Equations $$\frac{\partial(\rho_k \varepsilon_k)}{\partial t} + \nabla \cdot (\rho_k \varepsilon_k v_k) = \dot{m}_k \tag{T1}$$

$$\frac{\partial(\rho_k \varepsilon_k y_k^{jx})}{\partial t} + \nabla \cdot (\rho_k \varepsilon_k v_k y_k^{jx}) = \dot{m}_k^{jx} + r_k^{jx} \tag{T2}$$

Momentum Equations $$\frac{\partial(\rho_k \varepsilon_k v_k)}{\partial t} + \nabla \cdot (\rho_k \varepsilon_k v_k v_k) = \varepsilon_k \rho_k F_k + \nabla \cdot \bar{\bar{\tau}}_k + \sum_{\substack{m=l,g,s \\ m \neq k}} \beta_{km}(v_m - v_k) + \dot{m}_k v_k \tag{T3}$$

Fluctuating Energy Equation for the Particle ($\theta = 1/3 \cdot \langle C^2 \rangle$)

$$\frac{3}{2}\left[\frac{\partial}{\partial t}(\varepsilon_s \rho_s \theta) + \nabla \cdot (\varepsilon_s \rho_s v_s \theta)\right] = \bar{\bar{\tau}}_s : \nabla v_s - \nabla \cdot q - \gamma_s \tag{T4}$$

Constitutive Equations

1) Definitions $$\sum_{k=1}^{p} \dot{m}_k = 0, \quad \sum_{jx=1}^{n} r_k^{jx} = 0, \quad \sum_{jx=1}^{n} y_k^{jx} = 1.0, \quad \sum_{k=1}^{p} \varepsilon_k = 1.0 \tag{T5}$$

2) Equation of State $$\rho_{g,mixture} = \frac{P \bar{M}_{mixture}}{zRT} \tag{T6}$$

$$\text{where, } \bar{M}_{mixture} = \frac{1}{\displaystyle\sum_{jx=1}^{n} \frac{y_g^{jx}}{M^{jx}}} \tag{T7}$$

3) Stress Tensor $$\bar{\bar{\tau}}_k = \left[-P_k + \left(\lambda_k - \frac{2}{3}\mu_k\right)\text{tr}(\overline{D_k})\right]\bar{\bar{I}} + 2\mu_k \overline{D_k} \tag{T8}$$

$$\text{where, } \overline{D_k} = \frac{1}{2}[\nabla v_k + (\nabla v_k)^T] \tag{T9}$$

for Particle $$P_s = \rho_s \varepsilon_s \theta [1 + 2(1+e)g_o \varepsilon_s] \tag{T10}$$

$$\mu_s = \frac{2\mu_{sdil}}{(1+e)g_0}\left[1 + \frac{4}{5}(1+e)g_o\varepsilon_s\right] + \frac{4}{5}\varepsilon_s^2 \rho_s d_s g_o (1+e)\sqrt{\frac{\theta}{\pi}} \tag{T11}$$

$$\lambda_s = \frac{4}{3}\varepsilon_s^2 \rho_s d_s g_o (1+e)\sqrt{\frac{\theta}{\pi}} \tag{T12}$$

where, $g_0$ is the radial distribution function and $\mu_{sdil}$ is the particle phase dilute viscosity.

$$g_o = \left[1 - \left(\frac{\varepsilon_s}{\varepsilon_{s,max}}\right)^{1/3}\right]^{-1} \tag{T13}$$

$$\mu_{sdil} = \frac{5\sqrt{\pi}}{96}\rho_s d_s \theta^{1/2} \tag{T14}$$

4) Granular Conductivity of Fluctuating Energy ($q = -\kappa \nabla \theta$)

$$\kappa = \frac{2}{(1+e)g_0}\left[1 + \frac{6}{5}(1+e)g_o \varepsilon_s\right]^2 K_{dil} + 2\varepsilon_s^2 \rho_s d_s g_o (1+e)\sqrt{\frac{\theta}{\pi}} \tag{T15}$$

$$\text{where, } \kappa_{dil} = \frac{75}{384}\sqrt{\pi\rho_s}\, d_s \theta^{1/2} \tag{T16}$$

5) Collisional Energy Dissipation $$\gamma_s = 3(1-e^2)\varepsilon_s^2 \rho_s g_o \theta \left(\frac{4}{d_s}\sqrt{\frac{\theta}{\pi}} - \nabla \cdot v_s\right) \tag{T17}$$

6) Fluid-Particle Drag Coefficient $$\beta_B = 150\frac{\varepsilon_s^2 \mu_f}{\varepsilon_f^2 d_s^2} + 1.75\frac{\rho_f \varepsilon_s |v_f - v_s|}{\varepsilon_f d_s} \quad \varepsilon_f < 0.8 \tag{T18}$$

$$\beta_B = \frac{3}{4}C_d \frac{\rho_f \varepsilon_s |v_f - v_s|}{d_s}\varepsilon_f^{-2.65} \quad \varepsilon_f \geq 0.8 \tag{T19}$$

$$\text{where, } C_d = \frac{24}{\text{Re}_s}[1 + 0.15\text{Re}_s^{0.697}] \text{ for Re}_s < 1000 \tag{T20}$$

$$C_d = 0.44 \quad \text{for Re}_s \geq 1000 \tag{T21}$$

$$\text{Re}_s = \frac{\varepsilon_f \rho_f d_s |v_f - v_s|}{\mu_f} \tag{T22}$$

7) Particle-Particle Drag Coefficient $$\beta_{\substack{lm \\ l \neq m}} = \frac{3}{2}(1+e)\frac{\varepsilon_{sl}\rho_{sl}\varepsilon_{sm}\rho_{sm}(d_{sl}+d_{sm})^2}{\varepsilon_f(\rho_{sl}d_{sl}^3 + \rho_{sm}d_{sm}^3)}|v_l - v_m| \tag{T23}$$

8) External Forces
   :Continuous Phase $$F_f = \frac{g}{\varepsilon_f} \tag{T24}$$

:Particulate Phase $$F_k = \frac{g}{\varepsilon_f}\left(1 - \frac{1}{\rho_k}\sum_{m=l,g,s}\varepsilon_m \rho_m\right) \tag{T25}$$

9) Boundary Conditions for Particle
   :Velocity $$n \cdot \tau_c = -\frac{\sqrt{3\theta}\, \pi \Phi \rho_s \varepsilon_s g_0 U_{sl}}{6\varepsilon_{s,max}} \tag{T26}$$

:Granular Temperature $$-n \cdot q = -\frac{\sqrt{3\theta}\,\pi \Phi \rho_s \varepsilon_s g_0 |U_{sl}|^2}{6\varepsilon_{s,max}} + \frac{\sqrt{3}\,\pi \rho_s \varepsilon_s g_0 (1-e_w^2)\theta^{\frac{3}{2}}}{4\varepsilon_{s,max}} \tag{27}$$

TABLE 2

Syn-Gas Composition (CO-rich)

| | CO | CO$_2$ | H$_2$ | CH$_3$OH | H$_2$O | N$_2$ | Wax |
|---|---|---|---|---|---|---|---|
| Mol % | 51.00 | 13.00 | 35.00 | 0.0 | 0.0 | 1.00 | 0.0 |
| Wt % | 68.07 | 27.26 | 3.34 | 0.0 | 0.0 | 1.33 | 0.0 |

The invention claimed is:

1. A method of determining an optimum catalyst diameter from a plurality of potential catalyst diameters for use in a reactor facilitating contact between reactants in a bulk medium and catalyst particles for the production of reaction products, where the bulk medium is one of a gas, a liquid, or a gas-liquid and where the bulk medium transfers kinetic energy to the catalyst particles and the reactor maintains reaction promoting conditions, comprising the steps of:

expressing one or more mass transfer coefficients describing one or more mass transfers of the reactants from the bulk medium to the catalyst particles using, $$k_L = \frac{D_L \Theta^{1/4}}{(vd_p)^{1/2}} Sc^{1/3}$$

where:
$k_L$=one of the one or more mass transfer coefficients,
$D_L$=diffusivity coefficient of the one or more mass transfers from the bulk medium to the catalyst particles,
v=kinematic viscosity of the bulk medium and the catalyst particles,
θ=catalyst particle granular temperature,
Sc=Schmidt number, $v/D_L$,
$d_p$=dimension of the each potential catalyst diameter;

determining a plurality of potential catalyst diameters over a desired range;
determining a reactor production rate of reaction products based on the one or more mass transfer coefficients for each potential catalyst diameter in the plurality of potential catalyst diameters, by utilizing a hydrodynamic model of the reactor, the bulk medium, and the catalyst particle, where the hydrodynamic model determines a catalyst particle granular temperature and the hydrodynamic model determines the reactor production rate based on the one or more mass transfer coefficients; and
selecting an optimum diameter, where the optimum diameter is the one of the each potential catalyst diameter from the plurality of potential catalyst diameters that produces the maximum reactor production rate of reaction products.

2. The method of claim 1 wherein said granular temperature is substantially in the form of turbulence kinetic energy.

3. The method of claim 1 wherein:
at least one of the each potential catalyst diameter in the plurality of potential catalyst diameters is an effective catalyst particle diameter based upon the relationship between catalyst particle concentration and a coagulation coefficient for the catalyst particles.

4. The method of claim 1 wherein the bulk medium is an inert liquid, and the catalyst particles are in the form of a powder, and the inert liquid and the powder form a slurry.

5. The method of claim 1 wherein determining the reactor production rate includes the effect of a water-gas shift reaction.

6. The method of claim 1 wherein said reactor is a gas-solid, liquid-solid or gas-liquid-solid fluidized bed reactor.

7. The method of claim 1 wherein the reactor is a slurry bubble column reactor for producing methanol and other liquid hydrocarbon fuels from natural gas.

8. The method of claim 7 wherein the optimum catalyst diameter for reactor production of methanol and other liquid hydrocarbon fuels in the slurry bubble column reactor is in the range of 60-70 μm.

9. The method of claim 1 wherein the hydrodynamic model utilizes multi-phase computational fluid dynamics with the kinematic viscosity of the bulk medium as in input and where the hydrodynamic model is capable of computing hold-up and flow patterns for gas-liquid flow and gas-liquid-solids flow.

10. The method of claim 1 wherein determining a reactor production rate of reaction products for each potential catalyst diameter in the plurality of potential catalyst diameters includes selecting a plurality of particle concentrations, where the particle concentration is defined as the quantity of particles per unit volume of the bulk medium, and determining the reactor production rate of reaction products for the each potential catalyst diameter at each particle concentration in the plurality of particle concentrations.

11. The method of claim 10 where the optimum catalyst diameter is 20 μm to 120 μm.

12. A method of determining an optimum catalyst diameter from a plurality of potential catalyst diameters for use in a slurry bubble column reactor facilitating contact between synthesis gas compounds in a bulk medium and catalyst particles for the production of methanol and other hydrocarbon fuels, where the bulk medium transfers kinetic energy to the catalyst particles and the slurry bubble column reactor maintains reaction promoting conditions, comprising the steps of:

determining a plurality of potential catalyst diameters;
determining a slurry bubble column reactor production rate of methanol and other hydrocarbon fuels for each potential catalyst diameter in the plurality of potential catalyst diameters, by utilizing a hydrodynamic model of the slurry bubble column reactor, the bulk medium, and the catalyst particle, where the hydrodynamic model determines a catalyst particle granular temperature and the hydrodynamic model determines the slurry bubble column reactor production rate based on one or more mass transfer coefficients describing one or more mass transfers from the bulk medium to the catalyst particles, and correlating the catalyst particle granular temperature to the one or more mass transfer coefficients using, $$k_L = \frac{D_L \Theta^{1/4}}{(vd_p)^{1/2}} Sc^{1/3}$$

where:
$k_L$=one of the one or more mass transfer coefficients,
$D_L$=diffusivity coefficient of the one or more mass transfers from the bulk medium to the catalyst particles,
v=kinematic viscosity of the bulk medium and the catalyst particles,
θ=catalyst particle granular temperature,
Sc=Schmidt number, $v/D_L$,
$d_p$=dimension of the each potential catalyst diameter; and
selecting an optimum diameter, where the optimum diameter is the one of the each potential catalyst diameter from the plurality of potential catalyst diameters that produces the maximum slurry bubble column reactor production rate of methanol and other hydrocarbon fuels.

13. The method of claim 12 wherein at least one of the each potential catalyst diameter in the plurality of potential catalyst diameters is an effective catalyst particle diameter based upon the relationship between catalyst particle concentration and a coagulation coefficient for the catalyst particles.

14. The method of claim 12 wherein the hydrodynamic model utilizes multi-phase computational fluid dynamics with the kinematic viscosity of the bulk medium as in input and where the hydrodynamic model computes hold-up and flow patterns for gas-liquid flow and gas-liquid-solids flow.

15. The method of claim 12 wherein determining a reactor production rate of reaction products for each potential catalyst diameter in the plurality of potential catalyst diameters includes selecting a plurality of particle concentrations, where the particle concentration is defined as the quantity of particles per unit volume of the bulk medium, and determining the reactor production rate of reaction products for the each potential catalyst diameter at each particle concentration in the plurality of particle concentrations.

16. The method of claim 12 where the optimum catalyst diameter is 20 μm to 120 μm.

17. The method of claim 12 where the hydrodynamic model utilizes multi-phase computational fluid dynamics with the kinematic viscosity of the bulk medium as in input and where the hydrodynamic model computes hold-up and flow patterns for gas-liquid flow and gas-liquid-solids flow, wherein the slurry bubble column reactor is a Fischer-Tropsch reactor producing hydrocarbon fuels from syngas, and the catalyst particles are comprised of a Fischer-Tropsch catalyst.

18. The method of claim 17 wherein at least one of the each potential catalyst diameter in the plurality of potential catalyst diameters is an effective catalyst particle diameter based upon the relationship between catalyst particle concentration and a coagulation coefficient for the catalyst particles.

19. The method of claim 17 where the optimum catalyst diameter is 20 μm to 120 μm.

* * * * *